United States Patent
Bechtel et al.

(10) Patent No.: US 9,498,157 B2
(45) Date of Patent: Nov. 22, 2016

(54) ROBUST CALIBRATION AND SELF-CORRECTION FOR TISSUE OXIMETRY PROBE

(71) Applicant: ViOptix, Inc., Fremont, CA (US)

(72) Inventors: Kate LeeAnn Bechtel, Pleasant Hill, CA (US); Brian Wilfley, Los Altos, CA (US)

(73) Assignee: ViOptix, Inc., Fremont, CA (US)

( * ) Notice: Subject to any disclaimer, the term of this patent is extended or adjusted under 35 U.S.C. 154(b) by 105 days.

(21) Appl. No.: 13/887,152

(22) Filed: May 3, 2013

(65) Prior Publication Data

US 2013/0324816 A1 Dec. 5, 2013

Related U.S. Application Data

(60) Provisional application No. 61/642,389, filed on May 3, 2012, provisional application No. 61/642,393, filed on May 3, 2012, provisional application No. 61/642,395, filed on May 3, 2012, provisional application No. 61/642,399, filed on May 3, 2012, provisional application No. 61/682,146, filed on Aug. 10, 2012.

(51) Int. Cl.
*A61B 5/1455* (2006.01)
*A61B 5/1495* (2006.01)
*A61B 5/00* (2006.01)
*A61M 35/00* (2006.01)
*A61B 5/145* (2006.01)

(52) U.S. Cl.
CPC ......... *A61B 5/14552* (2013.01); *A61B 5/0075* (2013.01); *A61B 5/1455* (2013.01); *A61B 5/1495* (2013.01); *A61B 5/14546* (2013.01); *A61B 5/14551* (2013.01); *A61B 5/72* (2013.01); *A61B 5/7282* (2013.01); *A61B 5/74* (2013.01); *A61B 5/742* (2013.01); *A61B 5/7405* (2013.01); *A61B 5/7475* (2013.01); *A61M 35/003* (2013.01)

(58) Field of Classification Search
USPC .................................................. 600/310–344
See application file for complete search history.

(56) References Cited

U.S. PATENT DOCUMENTS 6,070,093 A * 5/2000 Oosta et al. ............... 600/316
2002/0019587 A1 * 2/2002 Cheng et al. ............ 600/322

\* cited by examiner

*Primary Examiner* — Tse Chen
*Assistant Examiner* — Marjan Fardanesh
(74) *Attorney, Agent, or Firm* — Aka Chan LLP

(57) ABSTRACT

A method for calibrating detectors of a self-contained, tissue oximetry device includes emitting light from a light source into a tissue phantom, detecting in a plurality of detectors the light emitted from the light source, subsequent to reflection from the tissue phantom, and generating a set of detector responses by the plurality of detectors based on detecting the light emitted from the light source. The method further includes determining a set of differences between the set of detector responses and a reflectance curve for the tissue phantom, and generating a set of calibration functions based on the set of differences. Each calibration function in the set of calibration functions is associated with a unique, light source-detector pair. The method further includes storing the set of calibration function in a memory of the self-contained, tissue oximetry device.

20 Claims, 12 Drawing Sheets

ROBUST CALIBRATION AND SELF-CORRECTION FOR TISSUE OXIMETRY PROBE

CROSS-REFERENCE TO RELATED APPLICATIONS

This patent application claims the benefit of U.S. provisional patent applications 61/642,389, 61/642,393, 61/642,395, and 61/642,399, filed May 3, 2012, and 61/682,146, filed Aug. 10, 2012, which are incorporated by reference along with all other references cited in this application.

BACKGROUND OF THE INVENTION

The present invention relates generally to optical systems that monitor oxygen levels in tissue. More specifically, the present invention relates to oximeters that include sources and detectors on sensor heads for emitting and detecting light.

Oximeters are medical devices used to measure oxygen saturation of tissue in humans and living things for various purposes. For example, oximeters are used for medical and diagnostic purposes in hospitals and other medical facilities (e.g., surgery, patient monitoring, or ambulance or other mobile monitoring for, e.g., hypoxia); sports and athletics purposes at a sports arena (e.g., professional athlete monitoring); personal or at-home monitoring of individuals (e.g., general health monitoring, or personal training for a marathon); and veterinary purposes (e.g., animal monitoring).

Pulse oximeters and tissue oximeters are two types of oximeters that operate on different principles. A pulse oximeter requires a pulse in order to function. A pulse oximeter typically measures the absorbance of light due to the pulsing arterial blood. In contrast, a tissue oximeter does not require a pulse in order to function, and can be used to make oxygen saturation measurements of a tissue flap that has been disconnected from a blood supply.

Human tissue, as an example, includes a variety of molecules that can interact with light via scattering or absorption (e.g., via light-absorbing chromophores). Such chromophores include oxygenated and deoxygenated hemoglobins, melanin, water, lipid, and cytochrome. Oxygenated and deoxygenated hemoglobins are the most dominant chromophores in the spectrum range of 600 nanometers to 900 nanometers. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving measurement accuracy; reducing measurement time; lowering cost; reducing size, weight, or form factor; reducing power consumption; and for other reasons, and any combination of these.

In particular, assessing a patient's oxygenation state is important as it is an indicator of the state of the patient's health. Thus, oximeters are often used in clinical settings, such as during surgery and recovery, where it may be suspected that the patient's tissue oxygenation state is unstable. For example, during surgery, oximeters should be able to quickly deliver accurate oxygen saturation measurements under a variety of non-ideal conditions. While existing oximeters have been sufficient for post-operative tissue monitoring where speed of measurement is less critical, existing oximeters fluctuate substantially and give inaccurate saturation measurements when used during surgery where various elements can interfere with accurate reading, such as if the oximeter comes in contact with blood.

Therefore, there is a need for improved oximeters and methods of making measurements using these oximeters.

BRIEF SUMMARY OF THE INVENTION

A sensor head for a compact oximeter sensor probe includes light sources and light detectors. A probe implementation is entirely self-contained, without any need to connect, via wires or wirelessly, to a separate system unit. The sources and detectors probe are arranged in a circular arrangement having various source-detector pair distances that allow for robust calibration and self-correction in a compact probe. Other source-detector arrangements are also possible.

According to a specific embodiment, a sensor head for a tissue oximetry device includes at least a first light source and a second light for generating and emitting light into tissue, and a set of detectors for detecting the light subsequent to reflection from the tissue. First and second detectors included in the set of detectors are positioned approximately 1.5 millimeters or closer to the first light source or the second light source, or both. Third and fourth detectors included in the set of detectors are positioned approximately 2.5 millimeters or farther from the first light source or the second light source, or both.

According to another specific embodiment, a sensor head for a tissue oximetry device includes a set of detectors positioned in a circular arrangement; and first and second light sources linearly positioned on a bisecting line of a circle of the circular arrangement. A first detector included in the set of detectors is nearest to the first light source relative to all other detectors in the set of detectors and is a first distance from the first light source. A second detector included in the set of detectors is nearest to the second light source relative to the all other detectors in the set of detectors and is a second distance from the second light source. The first distance and the second distance are equal.

According to another specific embodiment, a method for calibrating detectors of a tissue oximetry device includes emitting light from a light source into a tissue phantom, and detecting in a plurality of detectors the light emitted from the light source, subsequent to reflection from the tissue phantom. The method further includes generating a set of detector responses by the plurality of detectors based on detecting the light emitted from the light source, and comparing the set of detector responses with a reflectance curve for the tissue phantom. The method further includes generating a set of calibration functions based on the comparison. Each calibration function in the set of calibration functions is associated with a unique, first light source-detector pair. The method further includes storing the set of calibration functions in a memory of the tissue oximetry device. The steps of this specific embodiment may be repeated for one or more additional light sources of the tissue oximeter, and may be repeated for one or more additional tissue phantoms.

According to another specific embodiment, a method for calibrating detectors of a tissue oximetry device includes emitting light from a light source into a tissue phantom, wherein the light source is equidistance from a plurality of detectors; and detecting the light, which is reflected from the tissue phantom, in the plurality of detectors. The method also includes generating detector responses by each detector in the plurality of detectors based on detecting the light, which is reflected from the tissue phantom; and determining dissimilarities between the detector responses. The method also includes generating calibration functions based on the dissimilarities, wherein if the calibration functions are applied to the raw detector responses, the dissimilarities of the detector responses are equalized.

According to another specific embodiment, a method for operating a sensor head of a tissue oximetry device includes emitting light from a light source into tissue, wherein the light source is equidistance from a plurality of detectors; and detecting the light, which is reflected from the tissue, in the plurality of detectors. The method also includes generating detector responses by each detector in the plurality of detectors based on detecting the light, which is reflected from the tissue. The method also includes determining whether at least one of the detector responses for one of the detectors differs from the detectors response of others of the detectors by at least a threshold; and disregarding the at least one of the detector responses if the at least one of the detector responses for the one of the detectors differs from the detectors response of the others of the detectors by at least the threshold.

According to another specific embodiment, a method for calibrating the light sources of a tissue oximetry device includes emitting light from a first light source into tissue; and detecting in a first detector the light emitted by the first light source subsequent to reflection from the tissue. The first detector is a first distance from the first light source. The method also includes generating a first detector response based on detecting the light in the first detector. The method also includes emitting light from a second light source into the tissue; and detecting in a second detector the light emitted by the second light source subsequent to reflection from the tissue. The second detector is a second distance from the second light source, and the first distance and the second distance are equal. The method also includes generating a second detector response based on detecting in the second detector the light emitted by the second light source; and generating a calibration function that represents a dissimilarity between the first detector response and the second detector response if the first detector response and the second detector response are not equal.

The above described embodiments of the tissue oximetry device and the method of use enable robust detector calibration and provides for identification of local inhomogeneity in real tissue and for discarding reflectance data from moles or other tissue aberrations. The positioning of the detectors with respect to the light sources provides a relatively large number of unique source-to-detector distances that increase the probability that derived optical properties are accurate by decreasing reflectance data redundancy and also enables a fast, reliable correction for dissimilarities in the data caused by power differences between sources.

In an implementation, the device is a tissue oximeter, which can measure oxygen saturation without requiring a pulse or heart beat. A tissue oximeter of the invention is applicable to many areas of medicine and surgery including plastic surgery. The tissue oximeter can make oxygen saturation measurements of tissue where there is no pulse; such tissue, for example, may have been separated from the body (e.g., a flap) and will be transplanted to another place in the body.

Aspects of the invention may also applicable to a pulse oximeter. In contrast to a tissue oximeter, a pulse oximeter requires a pulse in order to function. A pulse oximeter typically measures the absorbance of light due to the pulsing arterial blood.

Other objects, features, and advantages of the present invention will become apparent upon consideration of the following detailed description and the accompanying drawings, in which like reference designations represent like features throughout the figures.

DETAILED DESCRIPTION OF INVENTION

Figure 1A:
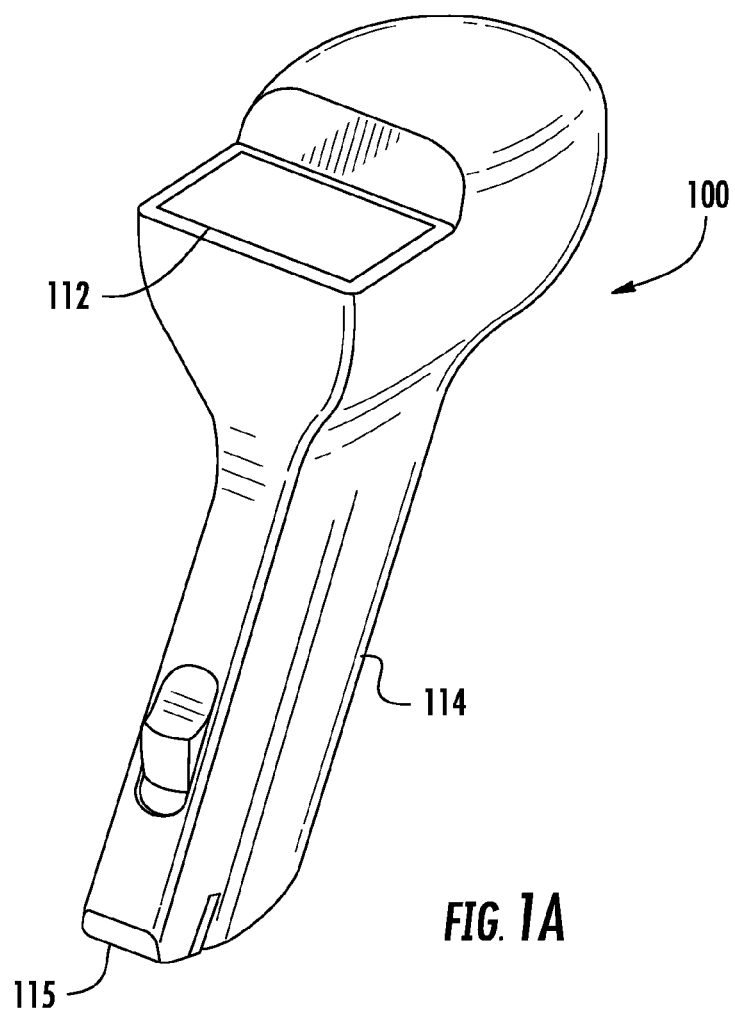
FIG. 1A illustrates a tissue oximetry device according to one embodiment.

Spectroscopy has been used for noninvasive measurement of various physiological properties in animal and human subjects. Visible light (e.g., red) and near-infrared spectroscopy is often utilized because physiological tissues have relatively low scattering in this spectral range. Human tissues, for example, include numerous chromophores such as oxygenated hemoglobin, deoxygenated hemoglobin, melanin, water, lipid, and cytochrome. The hemoglobins are the dominant chromophores in tissue for much of the visible and near-infrared spectral range. In the 700-900 nanometer range, oxygenated and deoxygenated hemoglobin have very different absorption features. Accordingly, visible and near-infrared spectroscopy has been applied to measure oxygen levels in physiological media, such as tissue hemoglobin oxygen saturation and total hemoglobin concentrations.

Various techniques have been developed for visible and near-infrared spectroscopy, such as time-resolved spectroscopy (TRS), frequency-domain techniques such as phase modulation spectroscopy (PMS), and continuous wave spectroscopy (CWS). In a homogeneous and semi-infinite model of physiological media, both TRS and PMS have been used to obtain the absorption coefficient and reduced scattering coefficient of the medium by use of the photon diffusion approximation or Monte Carlo models. From the absorption coefficients at multiple wavelengths, concentrations of oxygenated and deoxygenated hemoglobins can be determined and the tissue oxygen saturation calculated. CWS generally does not possess enough information to separate the effects of scattering and absorption. It has typically been used to solve a modified Beer-Lambert equation that requires assumptions about tissue scattering and two or more wavelengths are used ratiometrically to cancel out optical pathlength, which would otherwise be required to solve the equation. CWS, in its commonly-used form, provides relative oxygen saturation only and cannot provide absolute oxygen saturation or concentrations of oxygenated and deoxygenated hemoglobins.

Despite their capability of providing hemoglobin concentrations and absolute oxygen saturation, one major drawback of TRS and PMS is that the equipment is bulky and expensive. Another major drawback is that both of these techniques have difficulty measuring through relatively small volumes of tissue (i.e., "local" measurement, within a few millimeters). These techniques are typically used for "regional" measurements (minimum of 1 centimeter) due to the small time changes or phase shifts associated with short transit time through small volumes of tissue. In contrast, CWS may be manufactured at a lower cost, but is typically limited in its utility as described above unless enhancements are made by either including broadband spectral information or by including spatial information.

Spatially resolved spectroscopy (SRS) is one type of near-infrared spectroscopy that allows tissue absorption to be determined independently from tissue scattering, thereby allowing absolute measurements of chromophore concentrations.

More specifically, an SRS instrument emits light into tissue through a source and collects the diffusely reflected light at two or more detectors at different distances from the source. Alternatively, light may be emitted from two or more sources at different distances to one or more detectors. Scattering of light back to the detector is caused by relative changes in index of refraction of the tissue and includes Mie scattering from larger structures such as mitochondria (the majority of tissue scattering is a result of mitochondria) and Rayleigh scattering from smaller structures such as intracellular vesicles. Absorption of light is caused by interaction with chromophores. From the reflectance (recovered light intensity) as a function of distance from the source, an SRS instrument can quantify the absorption and scattering coefficients of tissue. The absorption coefficient at two or more wavelengths can provide oxygenated and deoxygenated hemoglobin concentrations and thereby tissue oxygen saturation within the volume of tissue interrogated. The wavelengths of the source(s) and the relative positions of the source(s) with respect to the detectors allow measurements to be made for a predetermined tissue depth.

One field in which near-infrared spectroscopy, such as SRS, is useful is in tissue flap surgery in which a tissue flap is moved from one location on a patient to another location for reconstructive surgery. Near-infrared spectroscopy techniques may be used to measure oxygen saturation in a tissue flap so that the viability of the tissue flap may be determined in surgery and after surgery. Intraoperative tissue flap oximetry probes that employ near-infrared spectroscopy must be able to quickly deliver accurate oxygen saturation measurements under a variety of non-ideal conditions. Current probes based on CWS have proven sufficient for postoperative tissue monitoring where speed of measurement is less critical and relative rather than absolute saturation measurements are of concern. However, currently available probes have been shown to give inaccurate saturation measurements when used intraoperatively due to common CWS assumptions. Embodiments of the presently described invention provide improvements in tissue oximetry over known devices and techniques briefly described above.

Tissue Oximetry Device

FIG. 1A is a simplified image of a tissue oximetry device 100 that is self-contained according to one embodiment. Tissue oximetry device 100 is configured to make tissue oximetry measurements, such as intraoperatively and postoperatively, without the need to communicate or interact with other devices. In an implementation, the device is handheld and can make tissue oximetry measurements and display these measurements, without needing to connect to another external component either via a cable or wirelessly. The electronics to make measurements and calculations is contained entirely within the housing of the handheld device. The device is a standalone handheld tissue oximeter probe, without a cable or wireless connection.

Tissue oximetry device 100 may be a handheld device that includes a tissue oximetry probe 115 (also referred to as a sensor head), which may be positioned at an end of a handle or sensing arm 114. Tissue oximetry device 100 is configured to measure the oxygen saturation of tissue by emitting light, such as near-infrared light, from tissue oximetry probe 115 into tissue, and collecting light reflected from the tissue at the tissue oximetry probe.

Tissue oximetry device 100 may include a display 112 or other notification device (e.g., a speaker) that notifies a user of oxygen saturation measured by the tissue oximetry device. While tissue oximetry probe 115 is described as being configured for use with tissue oximetry device 100, which is a handheld device, tissue oximetry probe 115 may be used with other tissue oximetry devices, such as a modular tissue oximetry device where the tissue oximetry probe is at the end of a cable device that couples to a base unit. The cable device might be a disposable device that is configured for use with one patient and the base unit might be a device that is configured for repeated use. Such modular tissue oximetry devices are well understood by those of skill in the art and are not described further.

Figure 1B:
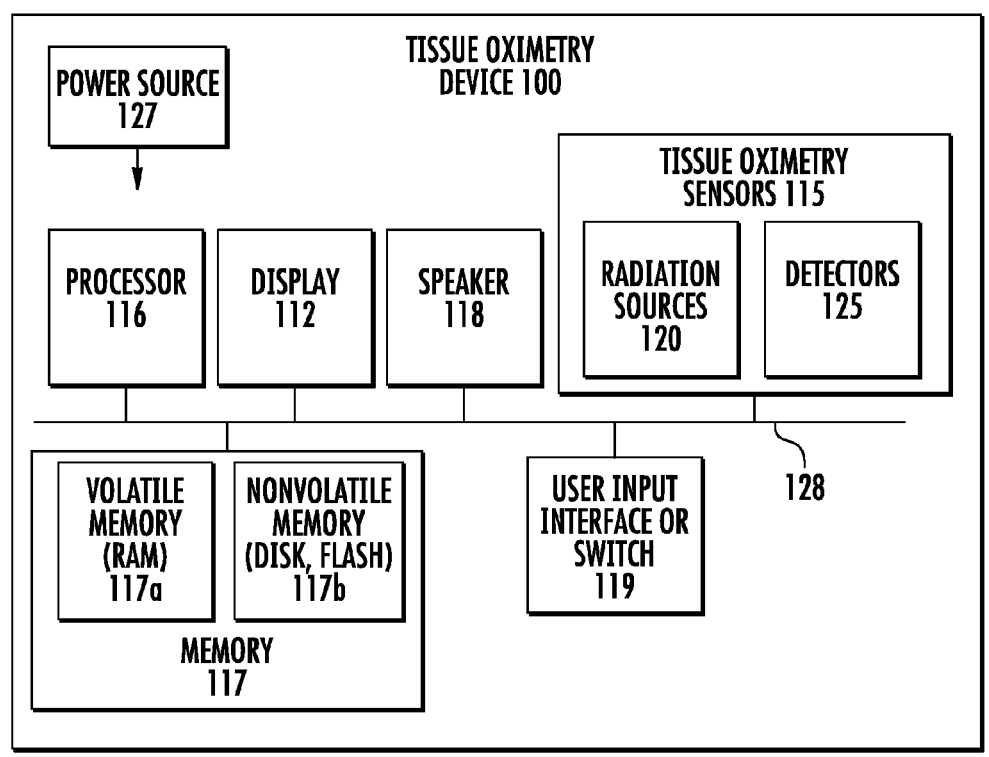
FIG. 1B is a simplified block diagram of the tissue oximetry device.

FIG. 1B is a block diagram of tissue oximetry device 100 according to one embodiment. Tissue oximetry device 100 includes display 112, a processor 116, a memory 117, a speaker 118, one or more user-selection devices 119 (e.g., one or more switches), a set of light sources 120, a set of detectors 125, and a power source (e.g., a battery) 127. The foregoing listed components may be linked together via a bus 128, which may be the system bus architecture of tissue oximetry device 100. Although this figure shows one bus that connects to each component, the busing is illustrative of any interconnection scheme serving to link these components or other components included in tissue oximetry device 100 subsystems. For example, speaker 118 could be connected to a subsystem through a port or have an internal direct connection to processor 116. Further, the components described are housed in a mobile housing (see FIG. 1A) of tissue oximetry device 100 according to at least one embodiment.

Processor 116 may include a microprocessor, a microcontroller, control logic, a multi-core processor, or the like. Memory 117 may include a variety of memories, such as a volatile memory 117a (e.g., a RAM), a non-volatile memory 117b (e.g., a disk, PROM, etc.). Different implementations of tissue oximetry device 100 may include any number of the listed components, in any combination or configuration, and may also include other components not shown.

Power source 127 can be a battery, such as a disposable battery. Disposable batteries are discarded after their stored charge is expended. Some disposable battery chemistry technologies include alkaline, zinc carbon, or silver oxide.

The battery has sufficient stored charged to allow use of the handheld device for several hours. After use, the handheld unit is discarded.

In other implementations, the battery can also be rechargeable where the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via an AC adapter with cord that connects to the handheld unit. The circuitry in the handheld unit can include a recharger circuit (not shown). Batteries with rechargeable battery chemistry may be sometimes used as disposable batteries, where the batteries are not recharged but disposed of after use.

Figure 2A:
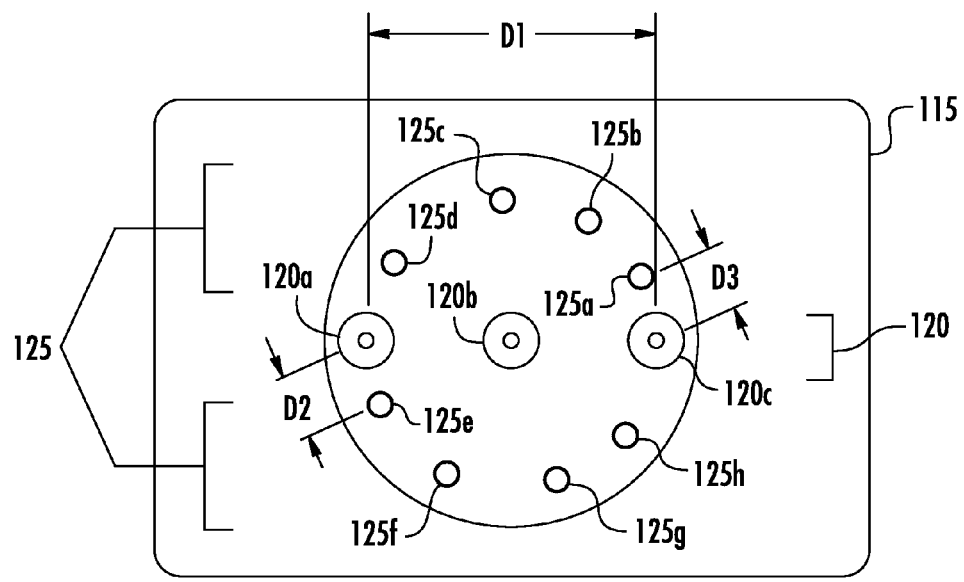
FIGS. 2A, 2B, and 2C are simplified end views of the tissue oximetry device.
Figure 2B:
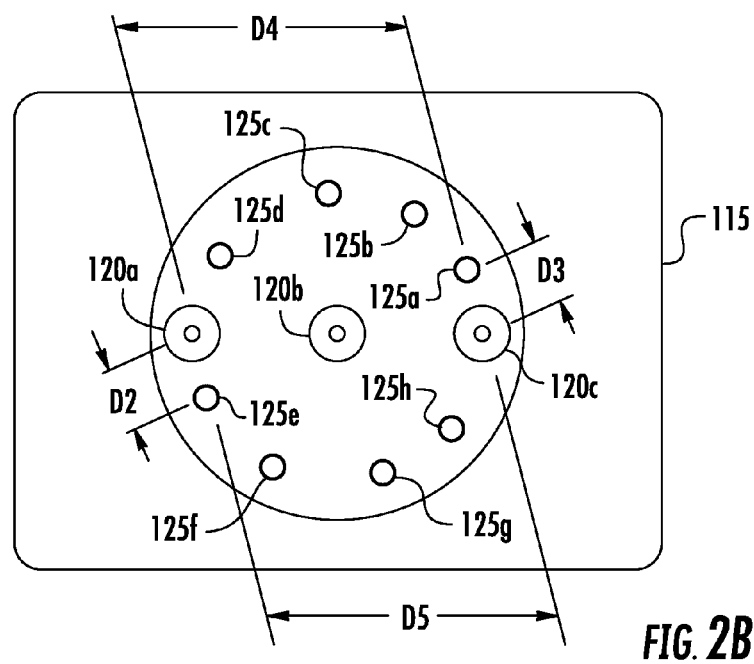
Figure 2C:
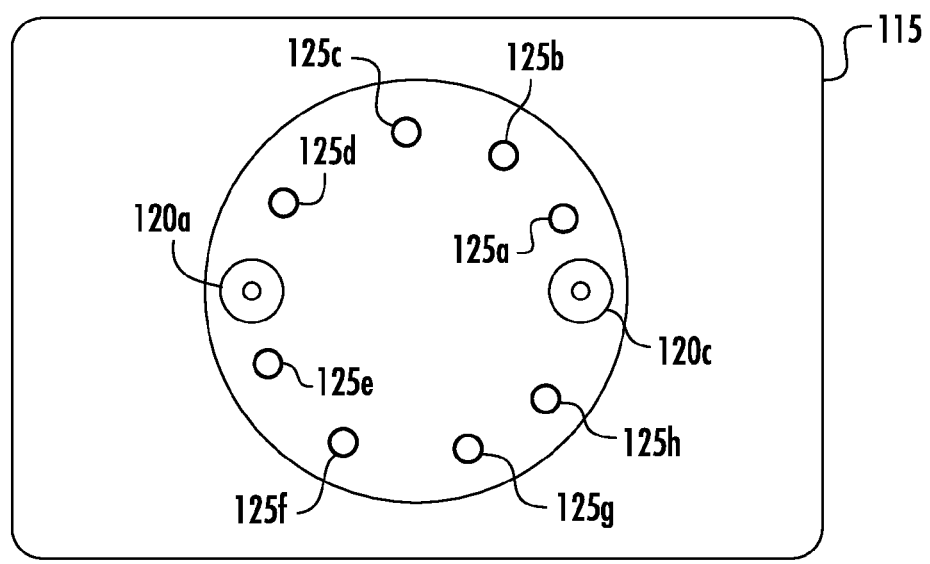

FIGS. 2A and 2B are simplified end views of tissue oximetry probe 115 according to one embodiment. The end views are the same but are marked differently for clarification. Tissue oximetry probe 115 is configured to contact tissue (e.g., a patient's skin) for which a tissue oximetry measurement is to be made. Tissue oximetry probe 115 includes the set of light sources 120 and includes the set of detectors 125. The set of light sources 120 may include two or more light sources. According to a specific implementation, tissue oximetry probe 115 includes three light sources 120a, 120b, and 120c, but according to other specific implementations includes two light sources, such as light sources 120a and 120c. The specific implementation of tissue oximetry probe 115 shown in FIGS. 2A and 2B includes the three light sources, 120a, 120b, and 120c whereas the specific implementation of tissue oximetry probe 115 shown in FIG. 2C includes fewer light sources. Specifically, tissue oximetry probe 115 shown in FIG. 2C has two light sources 120a and 120c, where light source 120b is omitted. Additional light sources (not shown) can be added.

Light sources 120 may be linearly positioned across tissue oximetry probe 115 and detectors 125 may be arranged in an arc or a circle (i.e., circular arrangement) on tissue oximetry probe 115. More specifically, light sources 120 may be arranged linearly, such as on a line (e.g., a diameter) that bisects a circle on which detectors 125 may be arranged. The outer light sources 120a and 120c are spaced a distance D1 apart where D1 may range from about 3 millimeters to about 10 millimeters. The central light source 120b may be positioned at an approximate mid point between outer light sources 120a and 120c and is substantially equidistantly (+/−10 microns) from each detector 125 where the distance between the central light source and each detector is about 1.5 millimeters to 5 millimeters. That is, the circle on which detectors 125 are arranged may have a diameter of about 3 millimeters to about 10 millimeters (e.g., 4 millimeters according to one specific embodiment). This maximum distance between the light sources and the detectors limits reflectance data to light that propagated within the top layer of tissue wherein little or no underlying subcutaneous fat or muscular layers prior contributes to the reflectance data generated by detectors 125 from light reflected from tissue. Propagation depth increases with increasing source-to-detector distance, with about 4-5 millimeters generally being a sufficient upper limit to ensure few detected photons propagated in lower tissue layers.

While detectors 125 are described as being arranged in an arc or circle, tissue oximetry device 100 may have other configurations of detectors, such as linear, square, rectangular, pseudo-random, or other arbitrary pattern.

The set of detectors 125 may include four or more detectors. According to a specific embodiment, the set of detectors 125 includes eight detectors 125a, 125b, 125c, 125d, 125e, 125f, 125g, and 125h as shown. Detectors 125 are solid state detectors and may be mounted to a PCB (not shown in FIGS. 2A-2C). Further, detectors 125 may be combined devices or discrete devices. Processor 116 is configured to control light sources 120 and detectors 125 via a set of electrical traces that run through the PCB. The circular configuration of detectors 125 and the linear arrangement of light sources 125 allows for a relatively simple arrangement of the electrical traces. For example, the electrical traces may radially extend outward from lights sources 120 and detectors 125 so that the electrical traces do not overlap in the PCB, which allows for relatively even spacing between the electrical traces and thereby provides for relatively low electrical crosstalk between the electrical traces. In some situations, relatively low crosstalk between the electrical traces lowers the signal-to-noise ratio of both the light sources 120 and the detectors 125 as compared to electrical traces that are alternatively arranged.

Detector Geometry for Increased Number of Data Points

In a specific implementation, detectors 125 are positioned with respect to outer light sources 120a and 120c such that four or more (e.g., fourteen) unique source-to-detector distances are created. With greater numbers of source-to-detector distances, this can be used to obtain greater accuracy, faster calibration, and redundancy (when duplicate source-to-detector distances are provided). At least two source-to-detectors distances are about 1.5 millimeters or less (e.g., 0.5 millimeters up to about 1.7 millimeters), and at least two more two source-to-detectors distances are about 2.5 millimeters or greater (e.g., 1.5 millimeters up to about 3.2 millimeters).

In other words, a first source-to-detector distance is about 1.5 millimeters or less. A second source-to-detector distance is about 1.5 millimeters or less. A third source-to-detector distance is about 2.5 millimeters or greater. A fourth source-to-detector distance is about 2.5 millimeters or greater. There can be various numbers of sources and detector arrangements to obtain these four source-to-detector distances, such as one source and four detectors, two sources and two detectors, one detector and four sources, or other arrangements and combinations.

For example, an implementation includes at least two sources and at least two detectors, where a maximum distance between a source and a detector is about 4 millimeters (or about 5 millimeters). At least two source-to-detector are about 2.5 millimeters or greater. At least two source-to-detector distances are about 1.5 millimeters or less.

When a greater number of sources and detectors are used, greater numbers of source-to-detector distances are available. As discussed, these can be used to provide greater accuracy, faster calibration, or redundancy, or a combination thereof. The arrangement of the sources and detectors can be in circular pattern, such as at points along the arc of a circle with radius (e.g., 4 millimeters, or 5 millimeters). In an implementation, a tolerance of the detector or source positions on the arc is within 10 microns of the arc curve. In other implementations, the tolerance is within about 0.25 millimeters.

The foregoing described source-to-detectors distances allow for the determination of the scattering coefficient and the absorption coefficient from the reflectance data generated by detectors 125. Specifically, reflectance data generated for detectors having relatively small source-to-detector distances (e.g., 1.5 millimeters or closer) is a function of the scattering coefficient of tissue and not the absorption coefficient, and reflectance data generated for detectors having relatively large source-to-detector distanced (e.g., 2.5 millimeters or farther) is a function of the $\mu_{\mathit{eff}}$ (inverse of the penetration depth), which is a function of both the scattering coefficient and the absorption coefficient. With at least two detectors 125 positioned at 1.5 millimeters or closer to at least one light source 120, and with at least two detectors positioned at 2.5 millimeters or farther from at least one light source 120, the scattering coefficient and the absorption coefficient may be independently determined.

According to one specific embodiment, sixteen unique source-to-detector distances are provided. The sixteen unique source-to-detector distances might be: 120*a*-125*d*=1.000 millimeters; 120*c*-125*h*=1.249 millimeters; 120*a*-125*e*=1.500 millimeters; 120*c*-125*a*=1.744 millimeters; 120*a*-125*c*=2.000 millimeters; 120*c*-125*g*=2.261 millimeters; 120*a*-125*f*=2.500 millimeters; 120*c*-125*b*=2.712 millimeters; 120*a*-125*b*=2.940 millimeters; 120*c*-125*f*=3.122 millimeters; 120*a*-125*g*=3.300 millimeters; 120*c*-125*c*=3.464 millimeters; 120*a*-125*a*=3.600 millimeters; 120*c*-125*e*=3.708 millimeters; 120*a*-125*h*=3.800 millimeters; and 120*c*-125*d*=3.873 millimeters where these distances may vary by about +/−10 microns.

In one alternative embodiment, the at least two source-to-detector distances are the same, such as the shortest source-to-detector distances. For example, the shortest source-to-detector distance D2 between light source 120*a* and detector 125*e*, and the shortest source-to-detector distance D3 between light source 120*c* and detector 125*a* may be the same. It follows that the source-to-detector distance D4 between light source 120*a* and detector 125*a*, and the source-to-detector distance D5 between light source 120*c* and detector 125*e* may also be the same. The source-to-detector distances D4 and D5 are the longest source-to-detector distance for light sources 120*a* and 120*c*. The foregoing description is for an example embodiment. For example, other pairs of source-to-detector distances might be the same, such as the next to shortest source-to-detector distances, and the next to longest source-to-detector distances.

With the exception of the shortest source-to-detector distance and the longest source-to-detector distance for light sources 120*a* and 120*c*, the source-to-detector distances for light sources 120*a* and 120*c* may be unique. As described above, tissue oximetry probe 115 may have fourteen unique source-to-detector distances that allow for fourteen data points to be collected by detectors 125 from light emitted from light sources 120*a* and 120*c*.

Furthermore, the source-to-detector distances for light sources 120*a* and 120*c* may also be selected such that the increases in the distances are substantially uniform. Thereby, a plot of source-to-detector distance verses reflectance detected by detectors 125 can provide a reflectance curve where the data points are substantially evenly spaced along the x-axis. These spacings of the distances between light sources 120*a* and 120*c*, and detectors 125 reduces data redundancy and can lead to the generation of relatively accurate reflectance curves.

Each light source 120 may include one or more light emitting diodes (LEDs), one or more laser diodes, one or more fiber optic cables, or a combination thereof. For example, each light source may include three or four LEDs 130 that are coupled to a printed circuit board (PCB, not shown in FIGS. 2A and 2B) that routes control signals to the LEDs. The LEDs included in one of the light sources 120 may generate and emit different wavelengths and the LEDs included in the respective light sources 120 may generate and emit the same sets of wavelengths. For example, the LEDs in light source 120*a* may generate and emit wavelengths of approximately 760 nanometers (e.g., +/−10 nanometers), 810 nanometers (e.g., +/−10 nanometers), and 850 nanometers (e.g., +/−20 nanometers), and the LEDs respectively included in light sources 120*b*, and 120*c* may each generate and emit these three wavelengths.

Figure 3A:
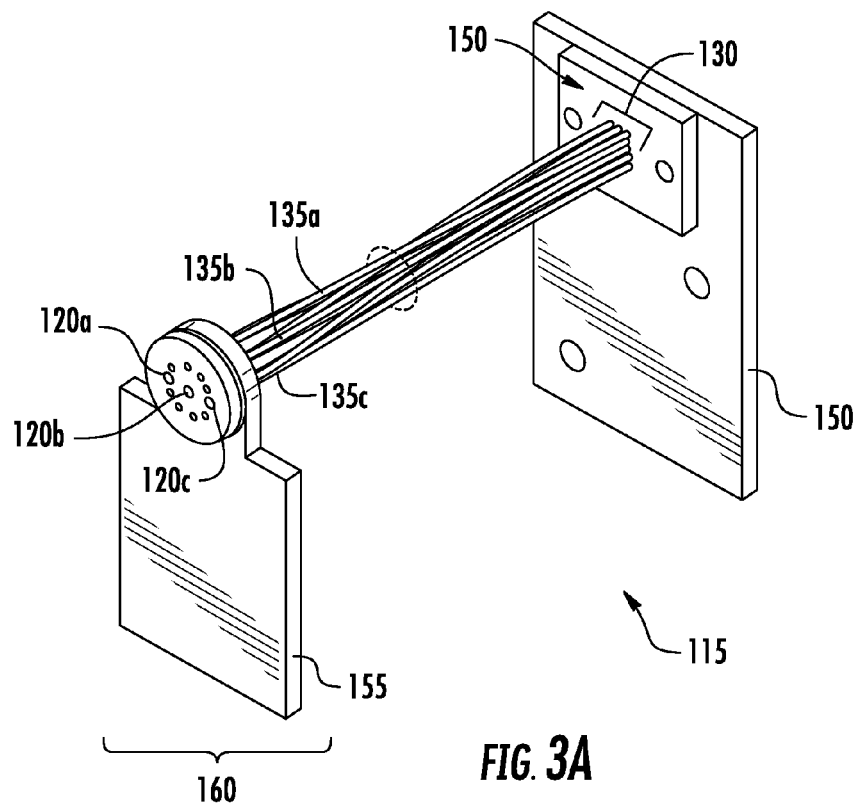
FIGS. 3A and 3B are a simplified perspective view and a cross-sectional view of the tissue oximetry probe, respectively.
Figure 3B:
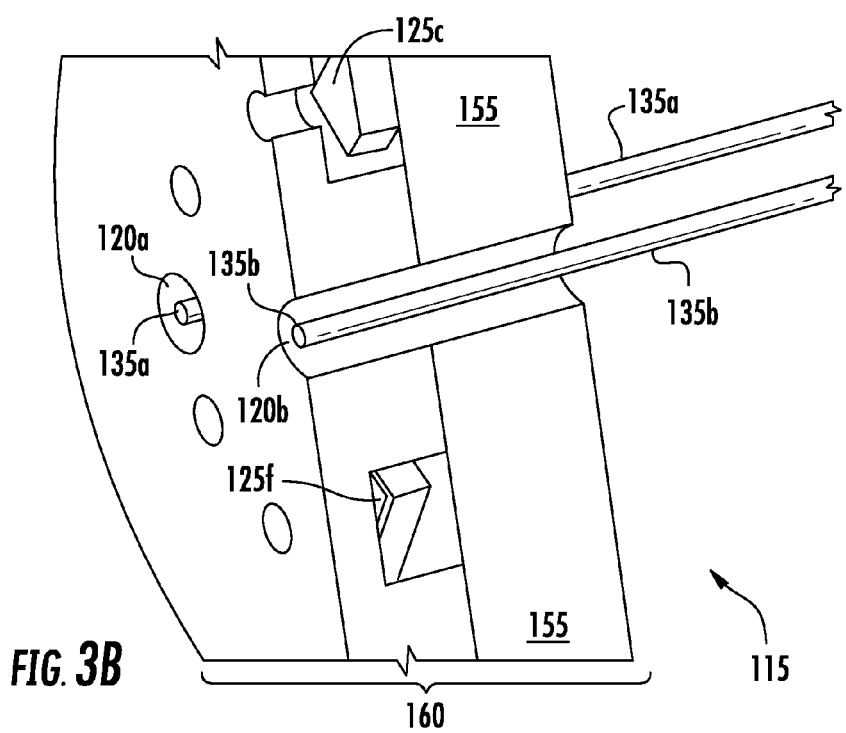

FIGS. 3A and 3B are, respectively, a simplified perspective view and a simplified cross-sectional view of tissue oximetry probe 115 according to one specific embodiment. According to the embodiment shown in FIGS. 3A and 3B, light sources 120*a*, 120*b*, and 120*c*, respectively, include sets of fiber optic cables 135*a*, 135*b*, and 135*c* (collectively fiber optic cables 135) and include a number of LEDs 130. Each set of fiber optic cables may include one or more fiber optic cables. According to an embodiment where each set of fiber optic cables includes more than one fiber optic cable, the fiber optic cables may be relatively narrow. LEDs 130 may be mounted on a back PCB 150 and each of the fiber optic cables 135 may be optically coupled to one or more of the LEDs to receive light from the LEDs and emit light from tissue oximetry device 100. For example, according to an embodiment where each light source 120 includes three LEDs 130 and one fiber optic cable 135, the fiber optic cable may be optically coupled to the three LEDs included in the light source and may receive light generated by the three LEDs for transmissions from tissue oximetry device 100.

Figure 4:
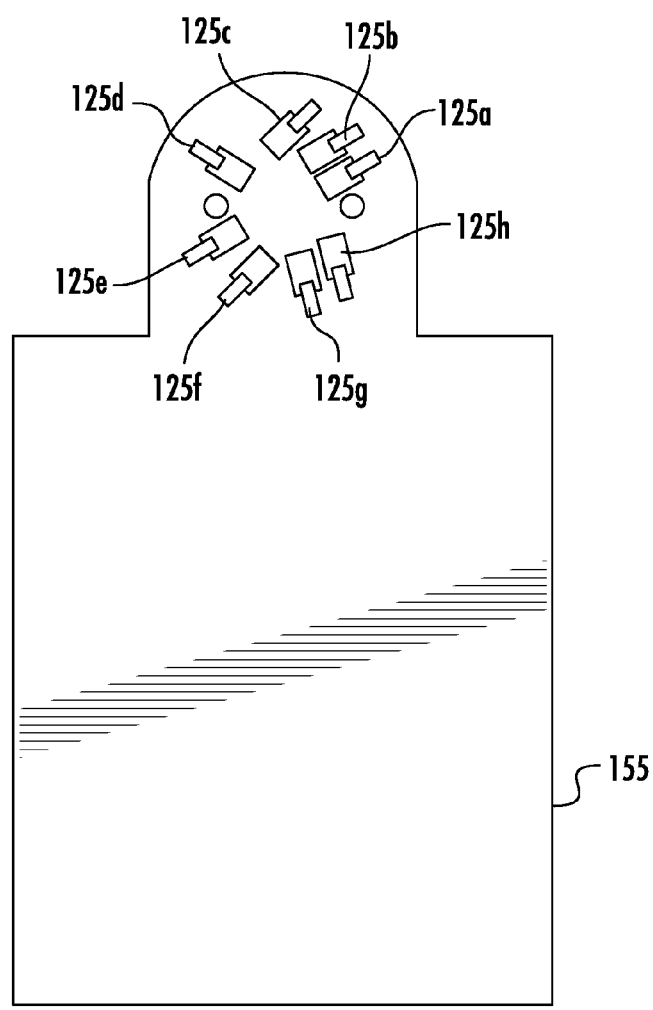
FIG. 4 is a simplified diagram of the front PCB with the detectors positioned in a circular arrangement on the PCB.

Detectors 125 may be mounted on the back PCB 150 or may be mounted on a front PCB 155. FIG. 4 is a simplified diagram of front PCB 155 showing detectors 125*a*-125*h* positioned in a circular arrangement on this PCB. As described above, the circular arrangement of detectors 125 allows for the electrical traces in PCB 155 or 150 to be routed in a relatively straightforward configuration. The traces can radiate outward from the detectors. This will minimize any crosstalk between the signals, since the interconnections do not have to cross over each other. The PCB can have fewer layers. Thus, this design reduces complexity, improves manufacturability and yield, reduces parasitics in the signal path, and reduces cost. The design supports the use of discrete components, such as discrete detectors 125 as compared to, for example, two or more detectors 125 integrated in a single unit or package. Discrete detectors can be less expensive to use or easier to source, or both. A circular arrangement of discrete detectors allows for a relatively large number of unique source-detector positions in a relatively compact space of a PCB.

If detectors 125 are mounted to back PCB 150, fiber optic cables (not shown) may optically couple a front section 160 of tissue oximetry probe 115 to the detectors where the fiber optic cables route detected light to the detectors. Front section 160 of tissue oximetry probe 115 may have a number of apertures formed therein for light to pass from sources 120 into tissue and to pass light reflected from the tissue to detectors 125. PCBs 150 and 155 may include one or more of a variety of connectors (e.g., edge connectors) that electrically couple the PCBs to other electronic circuits (e.g., a processor, a memory, the display, and others) in tissue oximetry device 100. While FIGS. 3A and 3B show an example embodiment of tissue oximetry probe 115 including three light sources 120*a*, 120*b*, and 120*c*, the tissue oximetry probe may include fewer light sources (e.g., 120*a* and 120*c*) or more light sources.

Figure 5A:
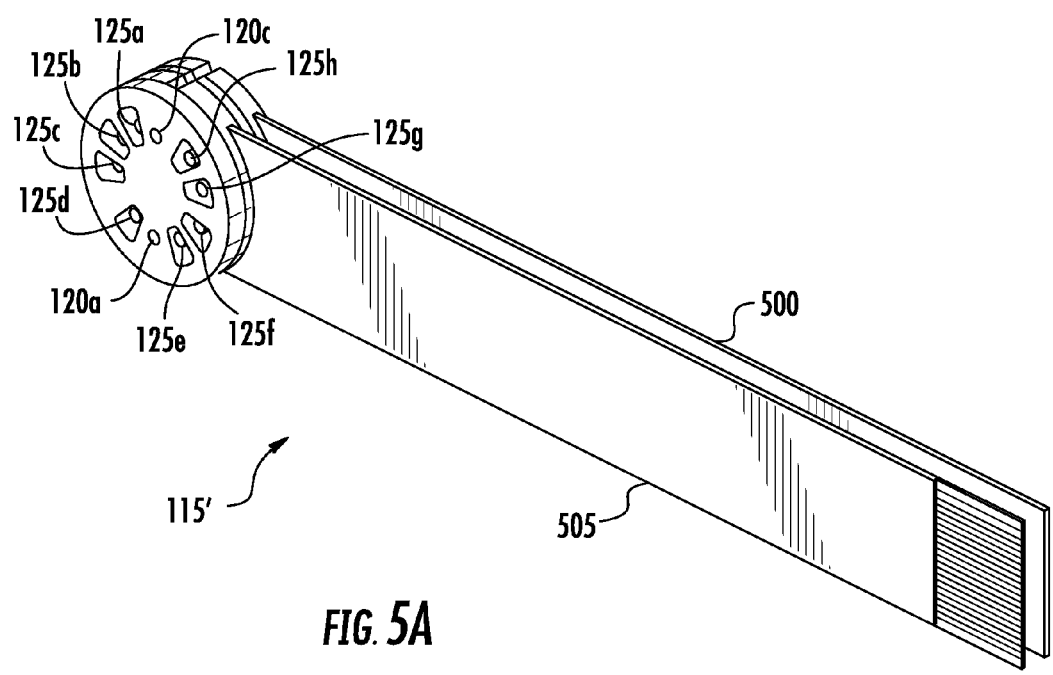
FIGS. 5A and 5B are a simplified perspective view and an exploded view, respectively, of a tissue oximetry probe according to another specific embodiment.
Figure 5B:
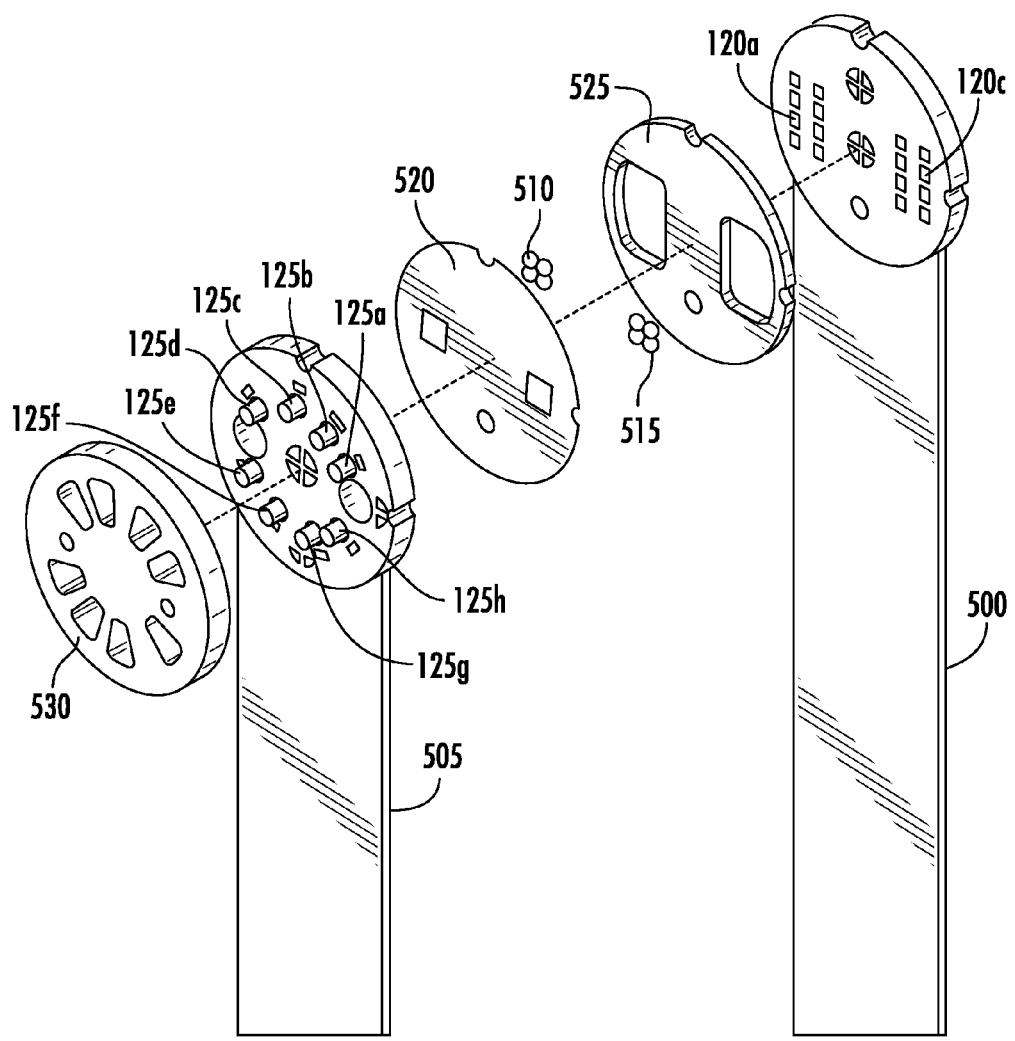

FIGS. 5A and 5B are a simplified perspective view and an exploded view, respectively, of a tissue oximetry probe 115′ according to another specific embodiment. The same numeral schema used for tissue oximetry probe 115 is used to identify the same or similar elements of tissue oximetry probe 115'. Tissue oximetry probe 115' is substantially similar to tissue oximetry probe 115 in that tissue oximetry probe 115' includes outer light sources 120a and 120c and the set of detectors 125 where outer light sources 120a and 120c and the set of detectors 125 have the same positions as in tissue oximetry probe 115. Tissue oximetry probe 115' differs from tissue oximetry probe 115 in that tissue oximetry probe 115' does not include central light source 120b.

Outer light sources 120a and 120b include one or more LEDs or laser diodes 130 (e.g., three LEDs) located on a back PCB 500. According to an embodiment where each outer light source includes three LEDs, the LEDs may emit wavelengths of approximately 760 nanometers, 810 nanometers, and 850 nanometers. Detectors 125 are located on a front PCB 505. PCBs 500 and 505 may include electrical traces for routing control signals to the outer sources and the detectors.

Two sets of lenses 510 and 515 may be positioned, respectively, over outer light sources 120a and 120c to direct light emitted from these light sources forward. More specifically, each set of lenses 510 and 515 may include one or more lenses to direct light emitted from outer light sources 120a and 120c forward. According to one specific embodiment, LEDs 130 are optically coupled to the lenses in a one-to-one manner where each lens directs the light emitted from one LED forward. The lenses may be hemispherical or the like. According to an alternative specific embodiment, a single lens directs the light from LEDs 130 forward.

Tissue oximetry probe 115' may include a lens plate 520 that holds the lenses in alignment for optimal forward direction of emitted light. Lens plate 520 may be connected to an LED aperture plate 525 that has one or more apertures formed therein for allowing light emitted from the outer light sources 120a and 120c to pass forward to the sets of lenses 510 and 515. Lens plate 520 may be connected to the back of front PCB 505, which may also have a number of apertures formed therein for allowing emitted light to pass forward. A contact plate 530 may be coupled to the front of front PCB 505 and may also have apertures formed therein for allowing emitted light to pass forward from tissue oximetry device 100, and to allow light reflected from tissue to pass to detectors 125.

Calibration of Sources and Detectors

Figure 6:
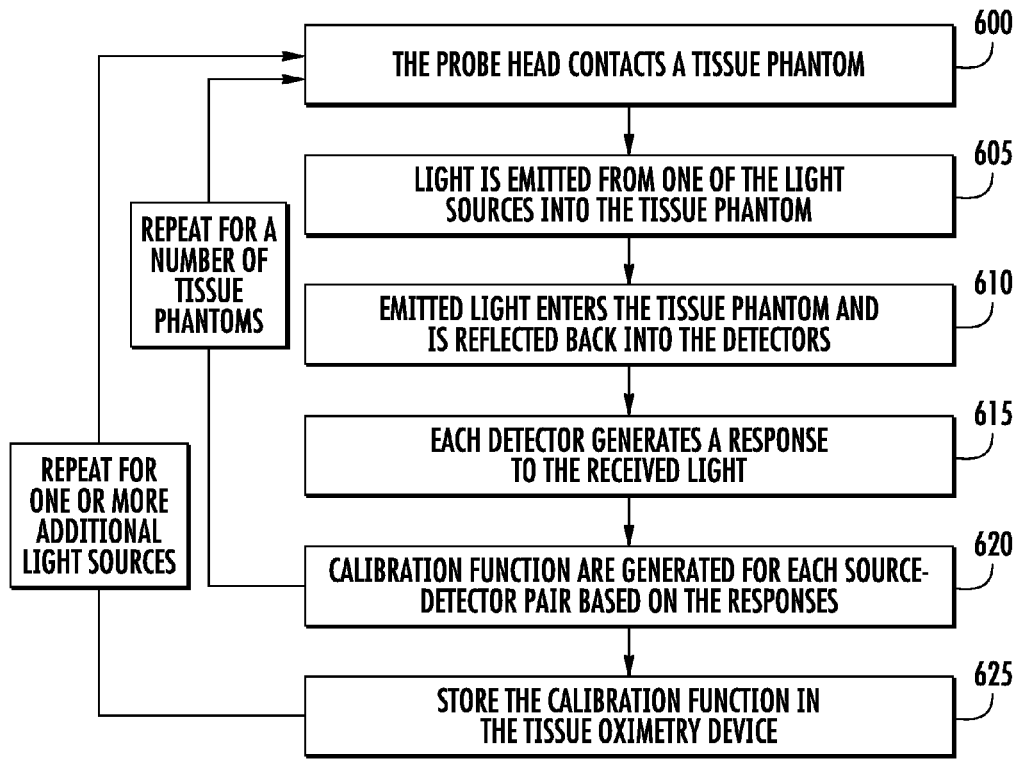
FIG. 6 is a high-level flow diagram of a method for calibrating each source-detector pair according to one embodiment.

FIG. 6 is a high-level flow diagram of a method for calibrating each source-detector pair according to one embodiment. The high-level flow diagram represents one example embodiment. Steps may be added to, removed from, or combined in the high-level flow diagram without deviating from the scope of the embodiment.

At 600, tissue oximetry probe 115 contacts a tissue phantom, which has homogeneous optical properties. Light (e.g., near-infrared light) is emitted from one or more of the light sources (e.g., outer light source 120a), step 605, into the tissue phantom and at least some of the light is reflected back by the tissue phantom. Each detector 125 receives a portion of the light reflected from the tissue phantom, step 610, and each detector generates reflectance data (i.e., a response) for the portion of reflected light received, step 615. The reflectance data for detectors 125 may not match a reflectance curve for the tissue phantom (i.e., may be offset from the reflectance curve). If the reflectance data generated by detectors 125 does not match the reflectance curve for the tissue phantom, the detectors may have an intrinsic gain or loss. The reflectance data generated is used by tissue oximetry device 100 to generate a set of calibration functions so that the raw reflectance data matches the reflectance curve for the tissue phantom, step 620. Raw reflectance data includes the reflectance data generated and output by the detectors prior to being utilized for determining the optical properties for the tissue and before being utilized for determining oxygen saturation for the tissue.

Steps 600 to 620 may be repeated for one or more tissue phantoms. The calibration function for each source-detector pair for each tissue phantom should generally be the same. However, if there is a deviation between the calibration functions for a given source-detector pair for a number of tissue phantoms, then the factors within the calibration function for the given source-detector might be averaged. Each of the calibration functions generated (including averaged functions) are stored in memory (e.g., Flash or other nonvolatile memory, or a programmable ROM), step 625.

Steps 600 to 625 may be repeated for each of the light sources, such as light source 120c. If steps 600 to 625 are repeated for light sources 120a and 120c, for example, then two calibration functions may be stored in memory for each detector, and each of the stored calibration functions for each detector is associated with one of the light sources. That is, each source-detector pair has a calibration function specifically for the source-detector pair. For example, detector 125a may have a first calibration function stored for light emitted from light source 120a (source-detector pair 125a-120a) and a second calibration function for light emitted from light source 120c (source-detector pair 125a-120c). Because a calibration function is stored for each source-detector pair, the calibration functions (e.g., two calibration functions) for each detector provide calibration not only for variations in the detectors but also for variations in the light sources. For example, the intrinsic gain or loss for a detector should not vary when receiving light from light source 120a or 120c. If the two calibration functions differ for a detector when receiving reflected light for light source 120a and thereafter for 120c, the difference in the reflectance data for a given tissue phantom is attributable to differences in the intensity of light emitted by light source 120a and 120c. The calibration functions may be applied to reflectance data that is generated by detectors 125 when tissue oximetry device 100 is used for oxygen saturation measurement in real tissue, for example, so that any intrinsic gains or losses of the detectors 125, and any difference in the intensity of light from light sources 125, may be compensated for. Specifically, the calibration functions are applied on a source-detector pair basis for the raw reflectance data generated by the detectors.

As described briefly above, central light source 120b may be substantially equidistant (+/−10 microns) from each of detectors 125 such that detectors 125 can be relatively easily calibrated using homogeneous tissue phantoms. The term "homogeneity" used with respect to a tissue phantom refers to the optical properties of a tissue phantom being substantially constant throughout the volume of the tissue phantom. For example, the absorption coefficient $\mu_a$ and the reduced scattering coefficient $\mu_s'$ of a tissue phantom may be referred to as being homogeneous (i.e., substantially constant) throughout the tissue phantom. This is in contrast to real tissue, which exhibits anisotropic optical properties stemming from the intrinsic alignment of collagen fibers and other biological factors as well as the spatial variances, which may stem from differing degrees of tissue components and oxygen saturation.

Figure 7:
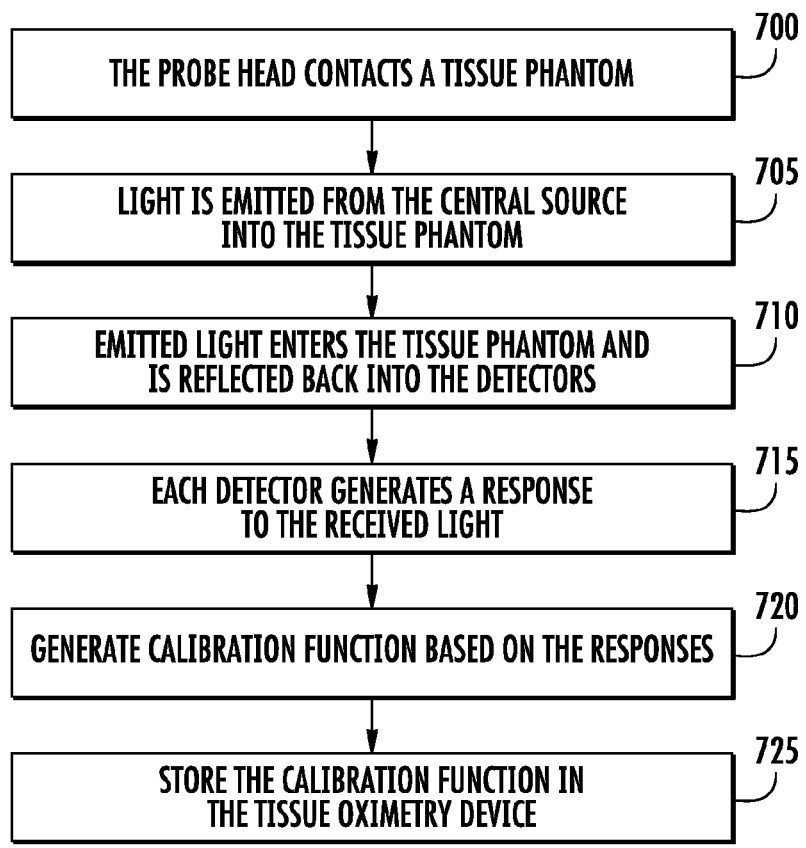
FIG. 7 is a high-level flow diagram for a method for calibrating the detectors according to one embodiment.

FIG. 7 is a high-level flow diagram of a method for calibrating detectors 125 according to one embodiment. The high-level flow diagram represents one example embodiment. Steps may be added to, removed from, or combined in the high-level flow diagram without deviating from the scope of the embodiment.

At 700, tissue oximetry probe 115 contacts a tissue phantom, which has homogeneous optical properties. Light (e.g., near-infrared light) is emitted from central light source 120b, step 705, into the tissue phantom and at least some of the light is reflected back by the tissue phantom. Each detector 125 receives the light reflected from the tissue phantom, step 710, and each detector generates a response to the reflected light, step 715. Each detector 125 should receive the same amount of reflected light due to the homogeneity of the tissue phantom. Any differences between detector responses can therefore be attributed to physical differences between the detectors. For example, one or more of the detectors may have an intrinsic gain or an intrinsic loss. The responses from detectors 125 are used by tissue oximetry device 100 to generate calibration functions for the detectors, where the calibration functions may be used by the tissue oximetry device to flatten the raw reflectance data (i.e., the responses) generated by the detectors to a single value, step 720. The calibration functions or the responses, or both, used for generating the calibration functions may be saved, e.g., in a local memory (e.g., a Flash or nonvolatile memory, or programmable ROM), step 725. The calibration functions may be applied to the raw reflectance data that are generated by detectors 125 when tissue oximetry device 100 is used to measure oxygen saturation levels in real tissue so that any intrinsic gains or losses of the detectors 125 may be compensated for.

Figure 8:
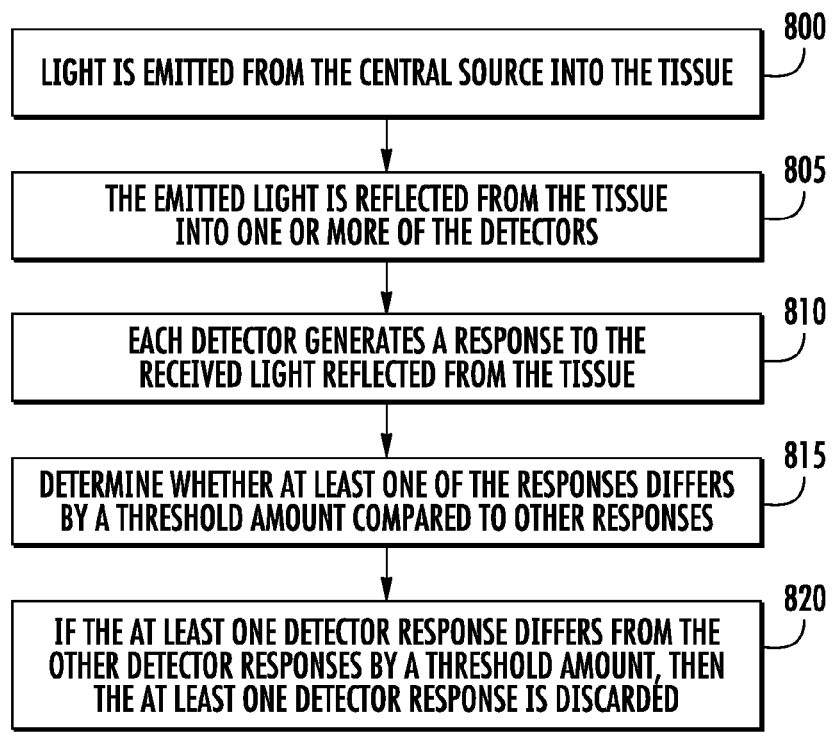
FIG. 8 is a high-level flow diagram for a method for detecting anomalies during use of the tissue oximetry device.

FIG. 8 is a high-level flow diagram of a method for detecting anomalies during use of tissue oximetry device 100 according to one embodiment. The high-level flow diagram represents one example embodiment. Steps may be added to, removed from, or combined in the high-level flow diagram without deviating from the scope of the embodiment.

Tissue oximetry device 100 may employ the method to detect anomalies such as significant, spatially congruous inhomogeneities in real tissue. Such an inhomogeneity can indicate the presence of a mole or type of tissue that does not contribute relevant information regarding the oxygenated hemoglobin and deoxygenated hemoglobin concentrations in a tissue flap, for example. The inhomogeneity could also indicate that part of the probe has gone beyond the edge of a wound or is covered by blood.

At 800, light (e.g., near-infrared light) is emitted from central light source 120b into tissue, and the light is reflected by the tissue into one or more of detectors 125, step 805. Each detector 125 generates a detector response to the received light, step 810. If one or more detectors lose contact with the tissue, then these detectors may generate a detector response, but the detector response might not be to light emitted from central light source 120b. Tissue oximetry device 100 may determine whether the difference in the light detected (i.e., detector response) by at least one of the detectors differs by a threshold amount compared to light detected by one or more of the other detectors, step 815.

If the detector responses to light emitted from central light source 120b differ between the detectors by the threshold amount (i.e., to a greater degree than predicted by ordinary tissue anisotropy), then the detector responses from the at least one detector in the clear minority of detector responses (i.e., detector response differs by at least the threshold amount) may be discarded, step 820, and not used to calculate oxygen hemoglobin and deoxygenated hemoglobin concentrations. The at least one detector in the clear minority may be assumed to have been positioned in contact with a mole, blood, or other or to have lost contact with the tissue.

According to one alternative, if the detector responses generated by a significant number (e.g., four) of detectors 125 differ significantly (e.g., by the threshold amount) from one another but there is no clear majority of detector responses, then tissue oximetry device 100 may disregard all of the detector responses and may indicate (e.g., on display 112) that accurate oxygen saturation cannot be determined for that currently probed region of tissue. The steps of the method may be repeated substantially continuously as tissue oximetry device 100 measures oxygen saturation in tissue. It is noted that central source 120b might not otherwise be used for obtaining contributive data for a reflectance curve used for determining oxygen saturation.

Self-Correction of Data During Oxygen Saturation Detection

Figure 9:
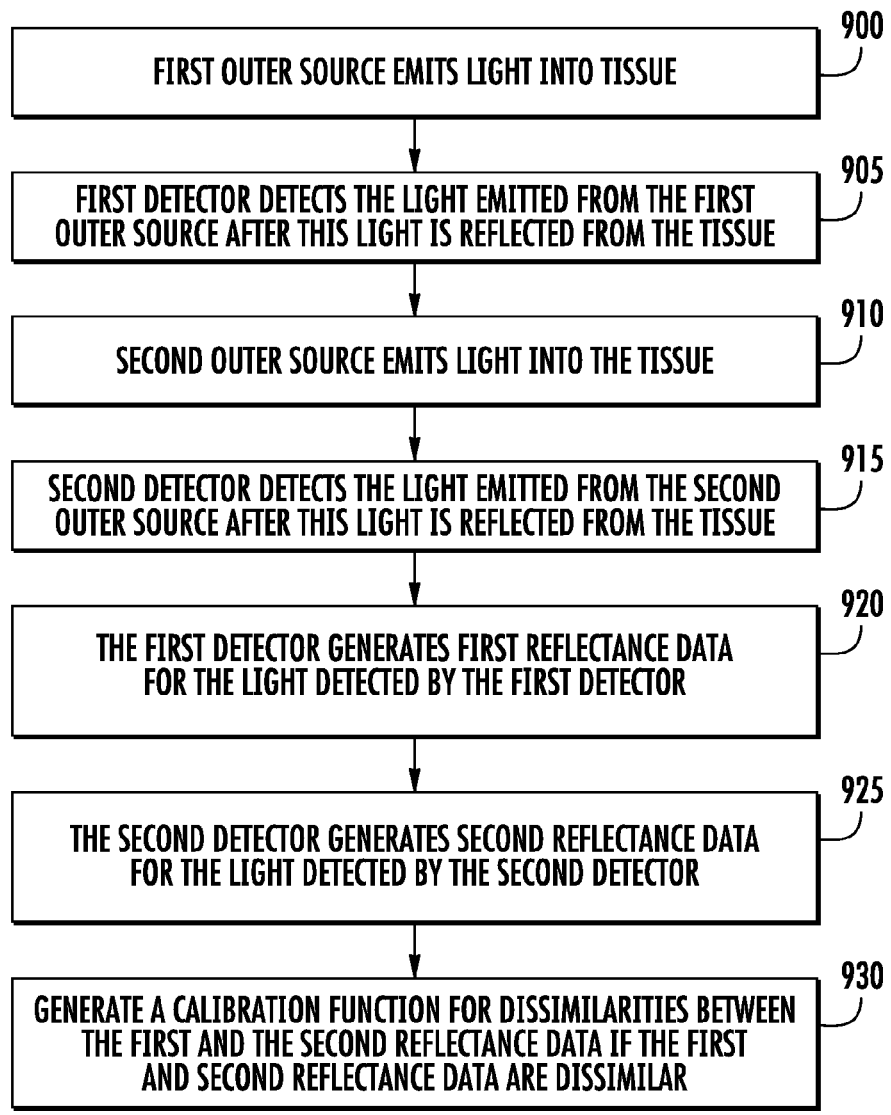
FIG. 9 is a high-level flow diagram for a method for calibrating the amount of light emitted by the outer sources during oxygen saturation measurements on tissue or with a tissue phantom.

FIG. 9 is a high-level flow diagram of a method for calibrating the amount of light emitted by outer sources 120a and 120c during oxygen saturation measurements on tissue or with a tissue phantom. The high-level flow diagram represents one example embodiment. Steps may be added to, removed from, or combined in the high-level flow diagram without deviating from the scope of the embodiment.

As described above, the shortest source-to-detector distances D2 and D3 are intentionally matched for the two outer sources 120a and 120c and the longest source-to-detector distances D4 and D5 are also intentionally matched for the two outer sources. With the shortest source-to-detector distances matched, when outer source 120a emits light, step 800, of a given wavelength into tissue and detector 125e detects this light reflected from the tissue, step 905, and when outer source 120c emits light into the tissue, step 910, and detector 125a detects this light reflected from the tissue, step 815, the reflectance data generated by detectors 125a and 125e, steps 920 and 925, respectively, should substantially match. That is, the amount of light detected by detectors 125a and 125e should substantially match.

Further, with the longest source-to-detector distances matched, when outer source 120a emits light of a given wavelength into tissue and detector 125a detects this light reflected from the tissue, and when outer source 120c emits light into the tissue and detector 125e detects this light reflected from the tissue, the reflectance data generated by detectors 125a and 125e should also substantially match. If these pairs of reflectance data do not match, then the source power of outer sources 120a and 120c and the amount of light emitted by these outer sources may also be mismatched.

According to one embodiment, the tissue oximetry device uses these pairs of reflectance data (if mismatched) generated by detectors 125a and 125e to correct the reflectance data generated by all of the detectors and to correct the oxygen saturation analysis performed by the device. More specifically, a calibration function, step 930, for the reflectance data (due to a source power difference between outer sources 120a and 120c) can be determined from the difference between the absolute reflectance detected by detectors 125a and 125e. This calibration function can be applied to the raw reflectance data generated by each detector 125 to compensate for the difference in the amount of light emitted by outer sources 120a and 120c. Specifically, two sets of reflectance data points that are offset from each other can be brought onto a single reflectance curve by applying the generated function to the reflectance data generated by each detector 125 thereby generating relatively more accurate oxygen saturation data.

Tissue oximetry device 100 may substantially continuously monitor and compare the reflectance data generated by detectors 125*a* and 125*e* to determine whether differences in the amount of light emitted from the two outer sources 120*a* and 120*c* occurs. Using the differences (if present), the reflectance data for each of detectors 125 can be substantially continuously corrected by tissue oximetry device 100 during oxygen saturation measurements. According to one alternative embodiment, the calibration of the outer sources is performed once and the generated function is stored for later use while making oxygen saturation measurements.

According to one alternative, additional or alternative source-to-detector distances can be matched for generating a function for the reflectance data due to source power difference between outer sources 120*a* and 120*c* (i.e., calibrating outer sources 120*a* and 120*c*). That is, the shortest or longest source-to-detector distances (or a combination of these) are not required for calibrating outer sources 120*a* and 120*c* and for correcting the reflectance data. Furthermore, while using two or more pairs of matched source-to-detectors distances may increase the reliability or accuracy of the source calibration, a single matched pair of source-to-detector distances may be used for calibrating outer sources 120*a* and 120*c*.

If a single matched pair of source-to-detector distances (e.g., D2 and D3) is used to calibrate outer sources 120*a* and 120*c* and for correcting the reflectance data, then the signal-to-noise ratio of the reflectance data may be relevant for selecting the particular source-to-detector distance to match. If minimal to low noise is present, then matching the longest source-to-detector distances may provide the most robust source calibration. However, noise may increase as the square root of the magnitude of a reflectance data measurement, and therefore may be significantly larger for longer source-to-detector distances. In this case, matching the shortest or relatively short source-to-detector distances may provide a more robust calibration of the outer sources and the reflectance data.

According to another alternative, all of the source-to-detector distances for the outer sources 120*a* and 120*c*, and the detectors 125*a*-125*h* are matched providing four matched source-to-detector distances. Matching four source-to-detector distances for outer sources 120*a* and 120*c* allows for the generation of two reflectance data sets for each outer source, which can be compared to verify accuracy of the reflection data.

The geometrical incorporation of fast and robust calibration, self-correction, and accurate data collection and processing methods limits fluctuations and inaccuracy seen in saturation measurements made by the intra-operative probes considered to be prior art. The previously discussed calibration, self-correction, and other features can lead to a fast, accurate tissue oximetry devices, which should be desirable to plastic surgeons involved in implant-based breast reconstruction and others concerned with detecting tissue regions in danger of necrosis in surgical environments.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method for calibrating detectors of a tissue oximetry device comprising:
    transmitting source electrical signals to a first light source and a second light source;
    transforming, by the first and second light sources, the electrical signals into light based on the source electrical signals, emitting light having at least two wavelengths into a first tissue phantom from a first source structure and a second source structure that are optically coupled respectively to the first and second light sources;
    detecting the light by a plurality of detector structures, subsequent to reflection from the first tissue phantom, wherein the plurality of detector structures comprises a first detector structure, a second detector structure, a third detector structure, and a fourth detector structure,
    the first and second source structures and the first, second, third, and fourth detector structures are arranged on a probe face of the tissue oximetry device,
    a first distance is from the first detector structure to the first source structure,
    a second distance is from the first detector structure to the second source structure,
    the first distance is greater than the second distance,
    a third distance is from the second detector structure to the first source structure,
    a fourth distance is from the second detector structure to the second source structure,
    the fourth distance is greater than the third distance,
    a fifth distance is from the third detector structure to the first source structure,
    a sixth distance is from the third detector structure to the second source structure,
    the fifth distance is different from the first distance and the second distance,
    the sixth distance is different from the first distance and the second distance,
    a seventh distance is from the fourth detector structure to the first source structure,
    an eighth distance is from the fourth detector structure to the second source structure,
    the seventh distance is different from the first, second, and fifth distances,
    the eighth distance is different from the first, second, fifth, and sixth distances,
    the first distance is greater than each of the second, third, sixth, seventh, and eighth distances, and
    the second distance is less than each of the fifth, sixth, seventh, and eight distances;
    generating digital reflectance data points for the first tissue phantom from detected light detected by the first, second, third, and fourth detector structures;
    comparing digital reflectance data points for a reflectance curve for the first tissue phantom and the digital reflectance data points for the first tissue phantom for the detected light detected by the first detector structure for the first and second distances, the second detector structure for the third and fourth distances, the third detector structure for the fifth and sixth distances, and the fourth detector structure for the seventh and eighth distances;
    generating a set of calibration functions based on comparing the digital reflectance data points for the reflectance curve for the first tissue phantom and the digital reflectance data points for the first tissue phantom for the detected light detected by the first detector structure for the first and second distances, the second detector structure for the third and fourth distances, the third detector structure for the fifth and sixth distances, and the fourth detector structure for the seventh and eighth distances, wherein each calibration function in the set of calibration functions is associated with a unique, source structure-detector structure pair; and storing the set of calibration functions in a memory of the tissue oximetry device.

2. The method of claim 1 wherein the first and second source structures and the first, second, third, and fourth detector structures are arranged in a circular arrangement on the probe face of the tissue oximetry device.

3. The method of claim 1 wherein the first and second, third, and fourth detector structures are arranged asymmetrically on a probe face of the tissue oximetry device.

4. The method of claim 1 wherein the first and second detector structures are arranged symmetrically about a point on a line.

5. The method of claim 4 wherein the third and fourth detector structures are arranged symmetrically about the point on the line.

6. The method of claim 5 wherein the first and second source structures and the first, second, third, and fourth detector structures are arranged in a circular arrangement and the line intersects a circle of the circular arrangement at two points.

7. The method of claim 1 wherein at least two source structure-to-detector structure distances are about 1.5 millimeters or less, and at least two source structure-to-detector structure distances are about 2.5 millimeters or greater.

8. The method of claim 7 wherein the source structure-to-detector structure distances are less than about 4 millimeters.

9. The method of claim 7 wherein the source structure-to-detector structure distances are less than about 10 millimeters.

10. The method of claim 1 wherein the first, second, third, and fourth detector structures are arranged in a circular arrangement and the first and second source structures are arrangement along a line that intersects that circle at two locations.

11. The method of claim 10 wherein the line bisects the circle.

12. The method of claim 10 wherein the line does not intersect detector locations of the detector structures on the circle.

13. The method of claim 1 wherein the second distance is the same as the third distance.

14. The method of claim 13 where the first distance is the same as the fourth distance.

15. The method of claim 1 wherein the second distance is approximately the same as the third distance.

16. The method of claim 15 wherein the first distance is approximately the same as the fourth distance.

17. The method of claim 1 comprising:
making an oxygen saturation measurement; and
correcting the oxygen saturation measurement using the set of calibration functions.

18. The method of claim 1 wherein each of the calibration functions comprises at least one factor.

19. The method of claim 18 comprising:
averaging the factors for the given one of the first, second, third, and fourth detector structures if the factors for the a given one of the first, second, third, and fourth detector structures differ by a threshold amount; and
storing an average of the factors in the memory.

20. A method comprising:
repeating the steps of claim 1 for at least a second tissue phantom, wherein the set of calibration functions are for the first tissue phantom and the second tissue phantom.

* * * * *